United States Patent
Haremza et al.

(10) Patent No.: US 6,737,527 B2
(45) Date of Patent: May 18, 2004

(54) 4-FORMYLAMINO-N-METHYLPIPERIDINE DERIVATIVES, THE USE THEREOF AS STABILIZERS AND ORGANIC MATERIAL STABILIZED THEREWITH

(75) Inventors: Sylke Haremza, Neckargemuend (DE); Jürgen Krockenberger, Stuttgart (DE); Manfred Appel, Landau (DE); Hubert Trauth, Dudenhofen (DE); Alexander Aumüller, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/239,213

(22) PCT Filed: Mar. 28, 2001

(86) PCT No.: PCT/EP01/03503

§ 371 (c)(1),
(2), (4) Date: Sep. 27, 2002

(87) PCT Pub. No.: WO01/74777

PCT Pub. Date: Oct. 11, 2001

(65) Prior Publication Data

US 2003/0083406 A1 May 1, 2003

(30) Foreign Application Priority Data

Apr. 4, 2000 (DE) ......................................... 100 16 379

(51) Int. Cl.⁷ .................... C07D 211/58; C07D 401/12; C07D 405/12
(52) U.S. Cl. ................... 546/186; 546/190; 546/191
(58) Field of Search ................................. 546/186, 183, 546/191, 192, 244

(56) References Cited

U.S. PATENT DOCUMENTS 5,171,328 A * 12/1992 Trauth et al. ................... 8/402

FOREIGN PATENT DOCUMENTS

EP    0 316 582    5/1989

* cited by examiner

*Primary Examiner*—Rita Desai
(74) *Attorney, Agent, or Firm*—Oblon, Spivak, McClelland, Maier & Neustadt, P.C.

(57) ABSTRACT

The present invention relates to 4-formylamino-N-methylpiperidine derivatives of the formula (I)

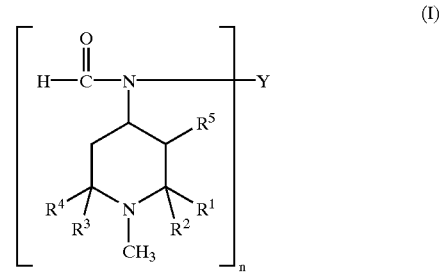

where the variables are as defined in the Description, to a process for preparing these piperidine derivatives, to the use of these piperidine derivatives of the invention, or prepared according to the invention, for stabilizing organic material, in particular for stabilizing plastics or coating materials, and also to the use of these piperidine derivatives of the invention, or prepared according to the invention, as light stabilizers or stabilizers for wood surfaces.

The present invention further relates to stabilized organic material which comprises these piperidine derivatives of the invention or prepared according to the invention.

19 Claims, No Drawings

4-FORMYLAMINO-N-METHYLPIPERIDINE DERIVATIVES, THE USE THEREOF AS STABILIZERS AND ORGANIC MATERIAL STABILIZED THEREWITH

CROSS-REFERENCE TO RELATED CASES

The present application is a National Stage (371) of PCT International Application PCT/EP01/03503, filed on Mar. 28, 2001, and claims priority to German Application No. DE 100 16 379.3, filed on Apr. 4, 2000.

The present invention relates to 4-formylamino-N-methylpiperidine derivatives of the formula (I)

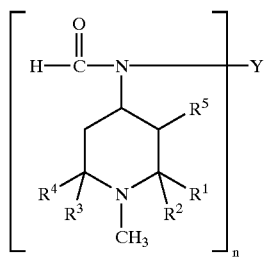

where $R^1$ to $R^5$, n and Y are as defined in the Description, to a process for preparing these piperidine derivatives, to the use of the piperidine derivatives of the invention, or prepared according to the invention, for stabilizing organic material, in particular for stabilizing plastics or coating materials, and also to the use of the piperidine derivatives of the invention, or prepared according to the invention, as light stabilizers or stabilizers for wood surfaces.

The invention further relates to stabilized organic material which comprises piperidine derivatives of the invention or prepared according to the invention.

2,2,6,6-Tetraalkylpiperidine derivatives are known light stabilizers for organic polymers. Their lack of compatibility with polyolefins and with other plastics, and also their incompatibility with acids or with materials which form acids when exposed to light and/or heat are frequently unsatisfactory, as are the duration of their protection action, the intrinsic color of the substances, and the thermal decomposition of the stabilizers during incorporation into polymers at elevated temperatures.

EP 0 316 582 describes piperidine derivatives in which these aspects of property profile have been improved, and which have the formula

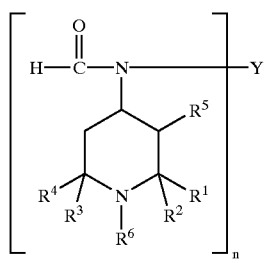

The definitions of $R^1$ to $R^5$, n and Y here are similar to those in the compounds of the formula I of the present invention.

$R^6$ embraces hydrogen and $C_1$–$C_{22}$-alkyl, besides a large number of other radicals. Line 14 of page 4 of EP 0 316 582 gives a particularly preferred definition of $R^6$, other than methyl, acetyl, cyanomethyl and aminoethyl, as hydrogen.

This is seen again in the compounds of Examples 1 to 48, where $R^6$ is without exception hydrogen. Only in the compounds of the final example (Example 49) does the nitrogen atom of the piperidine ring have an acetyl substituent.

Though the other aspects of the property profile of these stabilizers are good, their duration of stabilization is still frequently unsatisfactory.

It is an object of the present invention to provide stabilizers which give a further improvement in the duration of stabilization of organic material, and moreover have the above-mentioned advantageous properties of the known stabilizers, e.g. good compatibility with the materials to be stabilized, such as polyolefins or other plastics, a low level of intrinsic color, and stability during incorporation into the material to be stabilized.

We have found that this object is achieved, surprisingly, with the aid of the 4-formylamino-N-methylpiperidine derivatives of the formula (I)

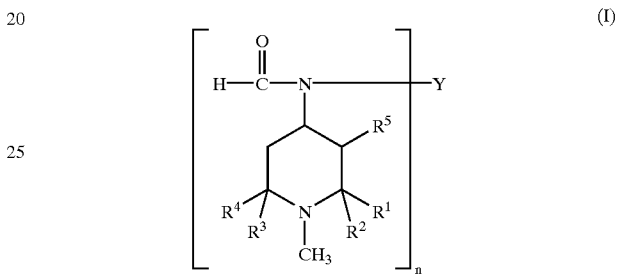

where
$R^1$, $R^2$, $R^3$ and $R^4$, independently of one another, are $C_1$–$C_4$-alkyl, or $R^1$ and $R^2$, or $R^3$ and $R^4$, together are tetramethylene or pentamethylene,
$R^5$ is hydrogen or $C_1$–$C_4$-alkyl, and
n is 1 or 2, with the proviso that
for n=1:
Y is hydrogen, $C_1$–$C_{22}$-alkyl, $C_2$–$C_{22}$-alkenyl, $C_3$-$Cl_2$-cycloalkyl, or bicycloalkyl, cyano-, hydroxyl- or $C_1$–$C_4$-alkoxycarbonyl-substituted $C_1$–$C_{22}$-alkyl, ethereal-oxygen-, nitrogen- or sulfur-interrupted, unsubstituted or hydroxyl-substituted $C_4$–$C_{22}$-alkyl, unsubstituted or $C_1$–$C_4$-alkyl-, fluorine-, chlorine-, $C_1$–$C_4$-alkoxy or di($C_1$–$C_4$-alkyl)amino-substituted $C_7$–$C_{22}$-phenyl- or diphenylalkyl, unsubstituted or $C_1$–$C_4$-alkyl- or $C_1$–$C_4$-alkoxycarbonyl-substituted phenyl, a radical of the formula

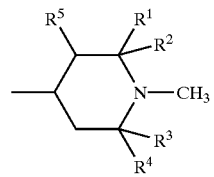

where $R^1$ to $R^5$, independently of one another, are as defined above,
or $C_1$–$C_{22}$-alkyl containing heterocyclic radicals, and
for n=2:
Y is $C_1$–$C_{22}$-alkylene, $C_5$–$C_{22}$-cycloalkylene, $C_8$–$C_{14}$-phenylalkylene, phenylene, or $C_4$–$C_{30}$-alkylene interrupted by ethereal oxygen, by nitrogen, by sulfur, or by five- or six-membered heterocycles.

The compounds of the invention have no intrinsic color, have good compatibility with a very wide variety of organic materials, in particular with organic polymers, have low vapor pressure and therefore low volatility, are resistant to thermal decomposition and to the action of acids, and their duration of stabilization is better than that of the prior art compounds.

Preferred compounds of this invention are those where $R^1$ to $R^4$ are methyl.

Other preferred compounds are those where $R^5$ is hydrogen.

If n is 1, radicals which may be used for Y, besides hydrogen, are:

i) $C_1$–$C_{22}$-alkyl, such as methyl, ethyl, n- or isopropyl, n-, sec- or isobutyl, n- or isopentyl, hexyl, octyl, decyl, dodecyl, octadecyl, pivalyl, 3,3-dimethylbut-2-yl, neopentyl, 4-methylpent-2-yl and 2-ethylhexyl;

ii) $C_2$–$C_{22}$-alkenyl, such as vinyl, allyl, butenyl, pentenyl and oleyl;

iii) $C_3$–$C_{12}$-cycloalkyl, such as cyclopropyl, cyclobutyl, cyclopentyl, cyclohexyl, methylcyclohexyl, cycloheptyl, cyclooctyl, cyclododecyl and bicycloheptyl, of which cyclopentyl and cyclohexyl are preferred; iv) cyano-, hydroxyl- or $C_1$–$C_4$-alkoxycarbonyl-substituted $C_1$–$C_{22}$-alkyl, such as cyanomethyl, hydroxyethyl, hydroxypropyl, hydroxybutyl, methoxycarbonylethyl and ethoxycarbonylethyl;

v) ethereal-oxygen-, nitrogen- or sulfur-interrupted, unsubstituted or hydroxyl-substituted $C_4$–$C_{22}$-alkyl, such as —(CH$_2$)$_3$N(CH$_3$)$_2$, —(CH$_2$)$_3$N(C$_2$H$_5$)$_2$, —(CH$_2$)$_3$—OCH$_3$, —(CH$_2$)$_3$—O—CH(CH$_3$)$_2$, —(CH$_2$)$_2$O—(CH$_2$)$_2$-OH, —CH$_2$—(CH$_2$)$_2$—CH$_2$—N(CH$_3$)$_3$, —(CH$_2$)$_2$—N[CH(CH$_3$)$_2$]$_2$, —(CH$_2$)$_2$—N(C$_2$H$_5$)$_2$, —(CH$_2$)$_2$N(CH$_3$)$_2$, —(CH$_2$)$_2$—OCH$_3$ and —(CH$_2$)$_2$OCH$_2$CH$_3$;

vi) unsubstituted or $C_1$–$C_4$-alkyl-, fluorine-, chlorine-, $C_1$–$C_4$-alkoxy- or di($C_1$–$C_4$-alkyl)amino-substituted $C_7$–$C_{22}$-phenyl- or diphenylalkyl, such as benzyl, methoxybenzyl, methylbenzyl, ethylbenzyl, isopropylbenzyl, trimethylbenzyl, fluorobenzyl, chlorobenzyl, methylenedioxybenzyl, phenylethyl, phenylpropyl and phenylbutyl, dimethylaminobenzyl, diphenylmethyl and 1,3-diphenylprop-2-yl;

vii) unsubstituted or $C_1$–$C_4$-alkyl- or $C_1$–$C_4$-alkoxycarbonyl-substituted phenyl, e.g. phenyl, tolyl and methoxy- and ethoxycarbonylphenyl;

viii) a radical of the formula

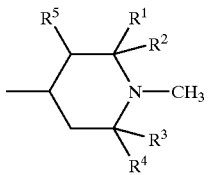

where $R^1$ to $R^5$ are as defined above, but in particular $R^1$ to $R^4$ are methyl, and in particular $R^5$ is hydrogen;

ix) $C_1$–$C_{22}$-alkyl containing heterocyclic radicals, for example

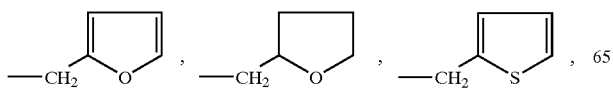

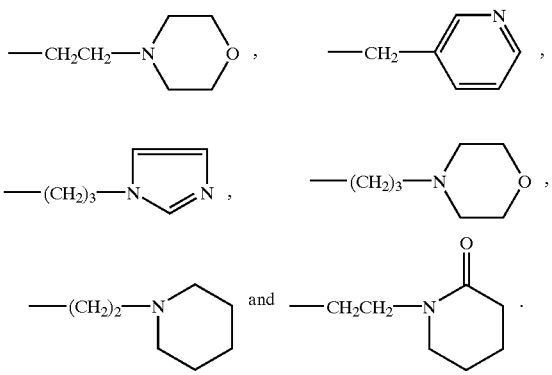

If n is 2, examples of radicals Y which may be used are:

x) $C_1$–$C_{22}$-alkylene and $C_5$–$C_{22}$-cycloalkylene, e.g. —(CH$_2$)$_o$—CH$_2$— where o is an integer from 1 to 21,

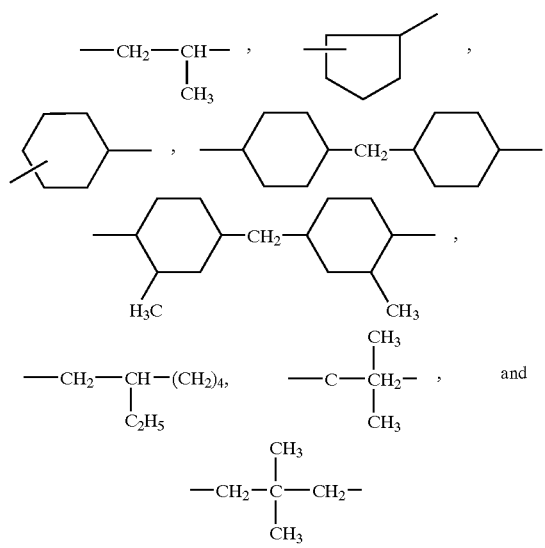

xi) $C_8$–$C_{14}$-phenylalkylene and phenylene, for example

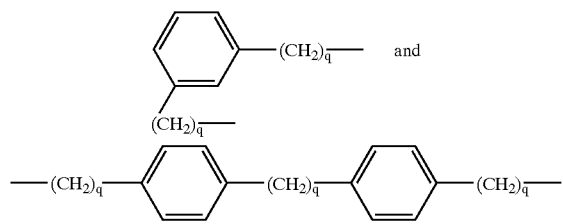

where q is 0, 1, 2, 3 or 4;

xii) $C_4$–$C_{30}$-alkylene interrupted by ethereal oxygen, by nitrogen, by sulfur or by five- or six-membered heterocycles, for example

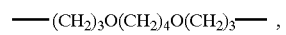

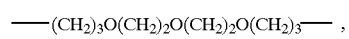

-continued

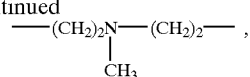

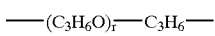

where r is an integer from 1 to 33,

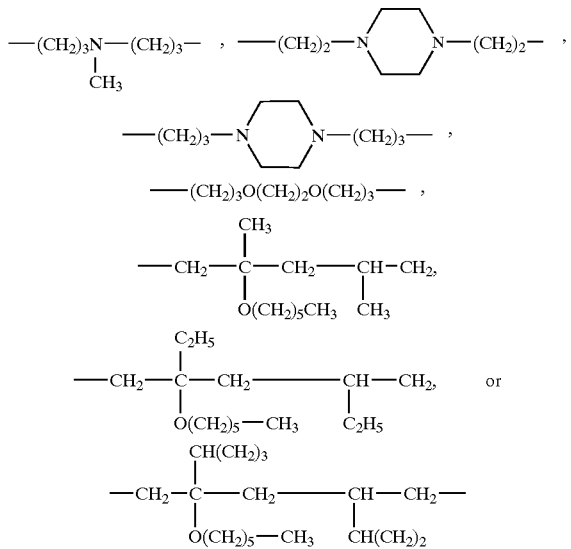

where s is 0, 1, 2, 3, 4, 5, 6 or 7.

Other preferred piperidine derivatives of the formula I are those where n is 2. The radicals Y are therefore bivalent bridges, examples of which have been indicated in the groups (x) to (xii) listed above.

Particularly preferred piperidine derivatives are those where Y is a bivalent $C_{12}$–$C_{22}$-alkylene bridge. In particular $C_1$-$Cl_2$-alkylene bridges may be used for Y.

The compounds of the invention which have the formula (I) may, as also described in EP 0 316 582, be prepared by reacting compounds of the formula (II)

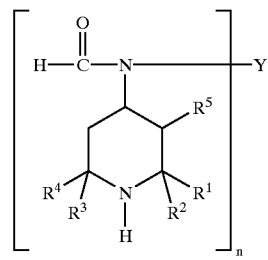

(II)

with formic acid or with formic esters, preferred esters being the methyl and ethyl esters. This process may be carried out with or without addition of a catalyst. These are especially Lewis acids, among which particular mention may be made of orthotitanic esters, specifically titanium orthobutylate.

Another path to the methylated compounds of the invention is provided by the reaction of the piperidine derivatives of the formula I'

(I')

where $R^1$ to $R^5$, n and Y are as defined for formula I, with methylating reagents, e.g. methyl halides, such as methyl chloride, bromide or iodide, or else dimethyl sulfate. These methylating reactions are familiar to the skilled worker and therefore require no further explanation.

A process for preparing pyridine derivatives of the formula I which is particularly elegant and is claimed as part of the present invention likewise starts with the compounds of the formula I' indicated above, which are reacted, in an organic solvent, emulsification medium or suspension medium (referred to below as "SESmedium") whose boiling point (at 1.013 bar) is at least 70° C., with formaldehyde, and then, at from 70° C. to not more than the boiling point (at 1.013 bar) of the SESmedium used, with formic acid.

Most of these starting amines are available commercially, for example Uvinul® 4050 H

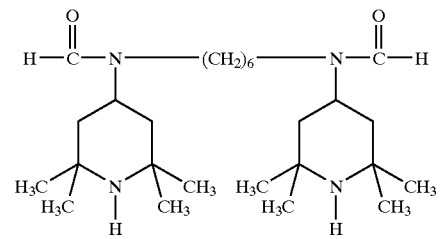

(BASF Aktiengesellschaft, Ludwigshafen). $R^1$ to $R^4$ of formula I are methyl here, $R^5$ is hydrogen, n is 2 and Y is a hexamethylene bridge.

For the purposes of the present invention, formaldehyde means not only the gaseous compound or its solution in water (formalin) but they specifically also mean those precursor compounds which readily liberate formaldehyde. Examples of these are the hemiacetals or acetals of formaldehyde with alkanols, e.g. methanol or ethanol, including therefore the compounds $H_2C(OH)(OCH_3)$, $H_2C(OCH_3)_2$, $H_2C(OH)(OC_2H_5)$ and $H_2C(OC_2H_5)_2$ and, where appropriate, mixtures of these.

Particularly suitable organic SESmedia with boiling point (at 1.013 bar) at least 70° C. are aromatic hydrocarbons, such as toluene, xylene and mixtures of these, mesitylene, and halo- and nitrohydrocarbons, e.g. chlorobenzene, the dichlorobenzenes, and nitrobenzene. Industrial mixtures of these aromatic compounds are of particular importance. Besides these, however, use may also be made of hydrocarbon mixtures free from aromatic compounds, if these mixtures have an appropriately high boiling point or boiling range.

The reaction of the compounds of the formula I' with formaldehyde in the first step usually takes place at from 0 to 80° C., preferably from 20 to 70° C., in particular at room temperature.

The molar ratio of N-H groups which are to be converted into N—$CH_3$ groups to formaldehyde is 1:1.25 to 1:2.5, i.e.

there is a molar excess of from 25 to 150% of formaldehyde. The molar ratio is usually about 1:2, i.e. formaldehyde is used in a 100 mol % excess over the amount needed for stoichiometric reaction.

The temperature at which the formaldehyde adduct reacts with formic acid is usually from room temperature to the boiling point (at 1.013 bar) of the SESmedium used, preferably from 40° C. to not more than the boiling point (at 1.013 bar) of the SESmedium used.

The water formed during the reaction is usefully removed by azeotropic distillation, and once the SESmedium has been separated off from the water of reaction, it may be reintroduced into the reaction mixture.

The reaction is usually carried out at atmospheric pressure (1.013 bar), but may also be carried out at subatmospheric pressure or with passage of an inert gas, e.g. nitrogen. This promotes the removal of the carbon dioxide produced during the reaction.

It should be mentioned here that the compounds of the invention and the compounds prepared according to the invention are usually used in the form of the free bases. However, these compounds may also be used in the form of the adducts which they form with acids. Examples of suitable anions in such cases are those derived from inorganic acids, and in particular from organic carboxylic acids, or else from organic sulfonic acids.

Examples of inorganic anions are chloride, bromide, sulfate, methosulfate, tetrafluoroborate, phosphate and thiocyanate.

Examples of carboxylic acid anions are formate, acetate, propionate, hexanoate, cyclohexanoate, lactate, and polycarboxylic acids having up to 3000 COOH groups.

Examples of sulfonic acid anions are benzenesulfonate and tosylate.

According to the invention, the piperidine derivatives of the formula I and the preferred embodiments thereof, and the piperidine derivatives prepared by the process of the invention, are used to render organic material resistant to degradation caused by light or heat. Mention should also be made here of their effectiveness as metal deactivators.

For the purposes of the present invention, organic materials are in particular plastics (used here synonymously with the term polymers) and coating materials, and also wood surfaces of any type.

The concentration in which the piperidine derivatives are added to the organic material to be stabilized, in particular to the plastics to be stabilized, is from 0.01 to 5% by weight, preferably from 0.02 to 1% by weight, based on the organic material. If the organic material is built up from molar molecules, as is the case, for example, in the preparation of plastics from the corresponding monomers, the addition may take place prior to, during or after the synthesis of the organic material.

If wood surfaces are to be protected, then for the purposes of the present invention the abovementioned concentrations of compounds of the invention and compounds prepared according to the invention are proportions by weight in appropriate wood-preservative formulations.

To mix the compounds of the invention, or the compounds prepared according to the invention, with the organic material, in particular with the plastics or coating materials, use may be made of any known apparatus and method for mixing stabilizers or other additives into organic materials, e.g. polymers.

The organic material, in particular plastics or coating materials, stabilized by the compounds of the invention, or the compounds prepared according to the invention, may, where appropriate, also comprise other additives, e.g. antioxidants, costabilizers, light stabilizers, metal deactivators, antistats, flame retardants, pigments or fillers.

Examples of antioxidants which may be added to the plastics alongside the compounds of the invention, or compounds prepared according to the invention, are compounds which can be classified in the following groups
a) alkylated monophenols,
b) alkylthiomethylphenols,
c) hydroquinones and alkylated hydroquinones,
d) tocopherols,
e) hydroxylated diphenyl thioethers,
f) alkylidenebisphenols,
g) O-, N- and S-benzyl compounds,
h) aromatic hydroxybenzyl compounds,
i) triazine compounds,
j) benzylphosphonates,
k) acylaminophenols,
l) esters of β-(3,5-di-tert-butyl-4-hydroxyphenyl)propionic acid, β-(5-tert-butyl-4-hydroxy-3-methylphenyl) propionic acid, β-(3,5-dicyclohexyl-4-hydroxyphenyl) propionic acid and 3,5-di-tert-butyl-4-hydroxyphenylacetic acid,
m) amides of β-(3,5-di-tert-butyl-4-hydroxyphenyl) propionic acid,
n) ascorbic acid and its derivates,
o) antioxidants based on amine compounds,
p) phosphites and phosphonites,
q) 2-(2'-hydroxyphenyl)benzotriazoles,
r) sulfur-containing peroxide scavengers and sulfur-containing antioxidants
s) 2-hydroxybenzophenones,
t) esters of unsubstituted or substituted benzoic acid,
u) acrylates,
v) sterically hindered amines,
w) oxamides and
x) 2-(2-hydroxyphenyl)-1,3,5-triazines.

Examples of alkylated monophenols of group a) are
2,6-di-tert-butyl-4-methylphenol,
2-tert-butyl-4,6-dimethylphenol, 2,6-di-tert-butyl-4-ethylphenol,
2,6-di-tert-butyl-4-n-butylphenol,
2,6-di-tert-butyl-4-isobutylphenol,
2,6-dicyclopentyl-4-methylphenol,
2-(α-methylcyclohexyl)-4,6-dimethylphenol,
2,6-dioctadecyl-4-methylphenol, 2,4,6-tricyclohexylphenol,
2,6-di-tert-butyl-4-methoxymethylphenol, nonylphenols which have a linear or branched side chain, such as
2,6-dinonyl-4-methylphenol,
2,4-dimethyl-6-(1'-methylundec-1'-yl)phenol,
2,4-dimethyl-6-(1'-methylheptadec-1'-yl)phenol,
2,4-dimethyl-6-(1'-methyltridec-1'-yl)phenol and mixtures of these compounds.

Examples of alkylthiomethylphenols of group b) are
2,4-dioctylthiomethyl-6-tert-butylphenol,
2,4-dioctylthiomethyl-6-methylphenol,
2,4-dioctylthiomethyl-6-ethylphenol and
2,6-didodecylthiomethyl-4-nonylphenol.

Examples of hydroquinones and alkylated hydroquinones of group c) are 2,6-di-tert-butyl-4-methoxyphenol,
2,5-di-tert-butylhydroquinone, 2,5-di-tert-amylhydroquinone,
2,6-diphenyl-4-octadecyloxyphenol, 2,6-di-tert-butylhydroquinone,
2,5-di-tert-butyl-4-hydroxyanisole,
3,5-di-tert-butyl-4-hydroxyanisole,
3,5-di-tert-butyl-4-hydroxyphenyl stearate and bis(3,5-di-tert-butyl-4-hydroxyphenyl)adipate.

Examples of tocopherols of group d) are a-tocopherol, β-tocopherol, γ-tocopherol, δ-tocopherol and mixtures of these compounds, and also tocopherol derivatives, such as tocopheryl acetate, tocopheryl succinate, tocopheryl nicotinate and tocopheryl polyoxyethylene succinate ("tocofersolate").

Examples of hydroxylated diphenyl thioethers of group e) are
2,2'-thiobis(6-tert-butyl-4-methylphenol),
2,2'-thiobis(4-octylphenol),
4,4'-thiobis(6-tert-butyl-3-methylphenol),
4,4'-thiobis(6-tert-butyl-2-methylphenol),
4,4'-thiobis(3,6-di-sec-amylphenol) and
4,4'-bis(2,6-dimethyl-4-hydroxyphenyl)disulfide.

Examples of the alkylidenebisphenols of group f) are
2,2'-methylenebis(6-tert-butyl-4-methylphenol),
2,2'-methylenebis-(6-tert-butyl-4-ethylphenol),
2,2'-methylenebis[4-methyl-6-(α-methylcyclohexyl)phenol],
2,2'-methylenebis(4-methyl-6-cyclohexylphenol),
2,2'-methylenebis(6-nonyl-4-methylphenol),
2,2'-methylenebis(4,6-di-tert-butylphenol),
2,2-ethylidenebis(4,6-di-tert-butylphenol),
2,2'-ethylidenebis(6-tert-butyl-4-isobutylphenol),
2,2'-methylenebis[6-(α-methylbenzyl)-4-nonylphenol],
2,2'-methylenebis[6-(α,α-dimethylbenzyl)-4-nonylphenol],
4,4'-methylenebis(2,6-di-tert-butylphenol), 4,4'-methylenebis-(6-tert-butyl-2-methylphenol), 1,1-bis(5-tert-butyl-4-hydroxy-2-methylphenyl)butane,
2,6-bis(3-tert-butyl-5-methyl-2-hydroxybenzyl)-4-methylphenol,
1,1,3-tris(5-tert-butyl-4-hydroxy-2-methylphenyl)butane,
1,1-bis(5-tert-butyl-4-hydroxy-2-methylphenyl)-3-n-dodecyl-mercaptobutane, ethylene glycol bis[3,3-bis(3'-tert-butyl-4'-hydroxyphenyl)butyrate],
bis(3-tert-butyl-4-hydroxy-5-methylphenyl) dicyclopentadiene, bis[2-(3'-tert-butyl-2'-hydroxy-5'-methylbenzyl)-6-tert-butyl-4-methylphenyl]-terephthalate, 1,1-bis(3,5-dimethyl-2-hydroxyphenyl)butane,
2,2-bis(3,5-di-tert-butyl-4-hydroxyphenyl)propane, 2,2-bis (5-tert-butyl-4-hydroxy-2-methylphenyl)-4-n-dodecylmercaptobutane and 1,1,5,5-tetrakis(5-tert-butyl-4-hydroxy-2-methylphenyl)-pentane.

Examples of O-, N- and S-benzyl compounds of group g) are
3,5,3',5'-tetra-tert-butyl-4,4'-dihydroxydibenzyl ether, octadecyl 4-hydroxy-3,5-dimethylbenzylmercaptoacetate, tridecyl
4-hydroxy-3,5-di-tert-butylbenzylmercaptoacetate,
tris(3,5-di-tert-butyl-4-hydroxybenzyl)amine,
bis(4-tert-butyl-3-hydroxy-2,6-dimethylbenzyl)
dithioterephthalate, bis(3,5-di-tert-butyl-4-hydroxybenzyl) sulfide and isooctyl 3,5-di-tert-butyl-4-hydroxybenzylmercaptoacetate.

Examples of aromatic hydroxybenzyl compounds of group h) are
1,3,5-tris(3,5-di-tert-butyl-4-hydroxybenzyl)-2,4,6-trimethylbenzene,
1,4-bis(3,5-di-tert-butyl-4-hydroxybenzyl)-2,3,5,6-tetramethylbenzene and 2,4,6-tris(3,5-di-tert-butyl-4-hydroxybenzyl)phenol.

Examples of triazine compounds of group i) are
2,4-bis(octylmercapto)-6-(3,5-di-tert-butyl-4-hydroxyanilino)-1,3,5-triazine,
2-octylmercapto-4,6-bis(3,5-di-tert-butyl-4-hydroxyanilino)-1,3,5-triazine,
2-octylmercapto-4,6-bis(3,5-di-tert-butyl-4-hydroxyphenoxy)-1,3,5-triazine,
2,4,6-tris(3,5-di-tert-butyl-4-hydroxyphenoxy)-1,2,3-triazine,
tris(3,5-di-tert-butyl-4-hydroxybenzyl) 1,3,5-isocyanurate,
tris(4-tert-butyl-3-hydroxy-2,6-dimethylbenzyl) 1,3,5-isocyanurate,
2,4,6-tris(3,5-di-tert-butyl-4-hydroxyphenylethyl)-1,3,5-triazine,
1,3,5-tris(3,5-di-tert-butyl-4-hydroxyphenylpropionyl) hexahydro-1,3,5-triazine, tris(3,5-dicyclohexyl-4-hydroxybenzyl)
1,3,5-isocyanurate and tris(2-hydroxyethyl) 1,3,5-isocyanurate.

Examples of benzylphosphonates of group j) are dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate and dioctadecyl
5-tert-butyl-4-hydroxy-3-methylbenzylphosphonate.

Examples of acylaminophenols of group k) are
4-hydroxylauroylanilide, 4-hydroxystearoylanilide and octyl
N-(3,5-di-tert-butyl-4-hydroxyphenyl)carbamate.

The propionates and acetates of group 1) are based on monohydric or polyhydric alcohols, such as methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide,
3-thiaundecanol, 3-thiapentadecanol, trimethylhexanediol, trimethylolpropane and
4-hydroxymethyl-1-phospha-2,6,7-trioxabicyclo[2.2.2] octane.

The propionamides of group m) are based on amine derivatives, such as N,N'-bis(3,5-di-tert-butyl-4-hydroxyphenylpropionyl)hexamethylenediamine,
N,N'-bis(3,5-di-tert-butyl-4-hydroxyphenylpropionyl) trimethylenediamine and N,N'-bis(3,5-di-tert-butyl-4-hydroxyphenylpropionyl)hydrazine.

Examples of ascorbic acid derivatives of group n) are ascorbyl palmitate, ascorbyl laurate and ascorbyl stearate, and also ascorbyl sulfate and ascorbyl phosphate, as well as ascorbic acid (vitamin C).

Examples of antioxidants of group o) based on amine compounds are
N,N'-diisopropyl-p-phenylenediamine,
N,N'-di-sec-butyl-p-phenylenediamine,
N,N'-bis(1,4-dimethylpentyl)-p-phenylenediamine,
N,N'-bis(1-ethyl-3-methylpentyl)-p-phenylenediamine,
N,N'-bis(1-methylheptyl)-p-phenylenediamine,
N,N'-dicyclohexyl-p-phenylenediamine,
N,N'-diphenyl-p-phenylenediamine,
N,N'-bis(2-naphthyl)-p-phenylenediamine,
N-isopropyl-N'-phenyl-p-phenylenediamine,
N-(1,3-dimethylbutyl)-N'-phenyl-p-phenylenediamine,
N-(1-methylheptyl)-N'-phenyl-p-phenylenediamine,
N-cyclohexyl-N'-phenyl-p-phenylenediamine,
4-(p-toluenesulfamoyl)diphenylamine,
N,N'-dimethyl-N,N'-di-sec-butyl-p-phenylenediamine, diphenylamine, N-allyldiphenylamine, 4-isopropoxydiphenylamine,
N-phenyl-1-naphthylamine, N-(4-tert-octylphenyl)-1-naphthylamine,
N-phenyl-2-naphthylamine, octyl-substituted diphenylamine, such as p,p'-di-tert-octyldiphenylamine,
4-n-butylaminophenol, 4-butyrylaminophenol, 4-nonanoylaminophenol,
4-dodecanoylaminophenol, 4-octadecanoylaminophenol,
bis(4-methoxyphenyl)amine,
2,6-di-tert-butyl-4-dimethylaminomethylphenol,
2,4-diaminodiphenylmethane, 4,4'-diaminodiphenylmethane,
N,N',N'-tetramethyl-4,4'-diaminodiphenylmethane,
1,2-bis[(2-methylphenyl)amino]ethane,
1,2-bis(phenylamino)propane, (o-tolyl)biguanide,
bis[4-(1',3'-dimethylbutyl)phenyl]amine, tert-octyl-substituted
N-phenyl-1-naphthylamine, a mixture of mono- and dialkylated tert-butyl/tert-octyldiphenylamine, a mixture of mono- and dialkylated nonyldiphenylamine, a mixture of mono- and dialkylated dodecyldiphenylamine, a mixture of mono- and dialkylated isopropyl/isohexyldiphenylamine, a mixture of mono- and dialkylated tert-butyldiphenylamine,
2,3-dihydro-3,3-dimethyl-4H-1,4-benzothiazine, phenothiazine, a mixture of mono- and dialkylated tert-butyl/tert-octylphenothiazine, a mixture of mono- and dialkylated tert-octylphenothiazine, N-allylphenothiazine,
N,N,N',N'-tetraphenyl-1,4-diamino-2-butene,
N,N-bis(2,2,6,6-tetramethylpiperidin-4-yl) hexamethylenediamine,
bis(2,2,6,6-tetramethylpiperidin-4-yl) sebacate,
2,2,6,6-tetramethyl-4-piperidinone and 2,2,6,6-tetramethyl-4-piperidinol.

Examples of the phosphites and phosphonites of group p) are triphenyl phosphite, diphenyl alkyl phosphite, phenyl dialkyl phosphite, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite,
bis(2,6-di-tert-butyl-4-methylphenyl) pentaerythritol diphosphite, diisodecyloxy pentaerythritol diphosphite,
bis(2,4-di-tert-butyl-6-methylphenyl) pentaerythritol diphosphite, bis(2,4,6-tris(tert-butylphenyl)) pentaerythritol diphosphite, tristearyl sorbitol triphosphite,
tetrakis(2,4-di-tert-butylphenyl) 4,4'-biphenylenediphosphonite,
6-isooctyloxy-2,4,8,10-tetra-tert-butyl-12H-dibenz[d,g]-1,3,2-dioxaphosphocine, 6-fluoro-2,4,8,10-tetra-tert-butyl-12-methyldibenz[d,g]-1,3,2-dioxaphosphocine, bis(2,4-di-tert-butyl-6-methylphenyl) methyl phosphite and bis(2,4-di-tert-butyl-6-methylphenyl) ethyl phosphite.

Examples of the 2-(2'-hydroxyphenyl)benzotriazoles of group q) are 2-(2'-hydroxy-5'-methylphenyl)benzotriazole,
2-(3',5'-di-tert-butyl-2'-hydroxyphenyl)benzotriazole,
2-(5'-tert-butyl-2'-hydroxyphenyl)benzotriazole,
2-(2'-hydroxy-5'-(1,1,3,3-tetramethylbutyl)phenyl)benzotriazole,
2-(31,5'-di-tert-butyl-2'-hydroxyphenyl)-5-chlorobenzotriazole,
2-(3'-tert-butyl-2'-hydroxy-5'-methylphenyl)-5-chlorobenzotriazole,
2-(3'-sec-butyl-5'-tert-butyl-2'-hydroxyphenyl)benzotriazole,
2-(2'-hydroxy-4'-octyloxyphenyl)benzotriazole,
2-(3',5'-di-tert-amyl-2'-hydroxyphenyl)benzotriazole,
2-(3',5-bis(α,α-dimethylbenzyl)-2'-hydroxyphenyl)benzotriazole, a mixture of
2-(3'-tert-butyl-2'-hydroxy-5'-(2-octyloxycarbonylethyl)phenyl)-5-chlorobenzotriazole,
2-(3'-tert-butyl-5'-[2-(2-ethylhexyloxy)carbonylethyl]-2'-hydroxyphenyl)-5-chlorobenzotriazole,
2-(3'-tert-butyl-2'-hydroxy-5'-(2-methoxycarbonylethyl)phenyl)-5-chlorobenzotriazole,
2-(3'-tert-butyl-2'-hydroxy-5'-(2-methoxycarbonylethyl)phenyl)benzotriazole,
2-(3'-tert-butyl-2'-hydroxy-5'-(2-octyloxycarbonylethyl)phenyl)benzotriazole,
2-(3'-tert-butyl-5'-[2-(2-ethylhexyloxy)carbonylethyl]-2'-hydroxyphenyl)benzotriazole,
2-(3'-dodecyl-2'-hydroxy-5'-methylphenyl)benzotriazole and
2-(3'-tert-butyl-2'-hydroxy-5'-(2-isooctyloxycarbonylethyl) phenylbenzotriazole,
2,2'-methylenebis[4-(1,1,3,3-tetramethylbutyl)-6-benzotriazol-2-ylphenol]; the product of complete esterification of
2-[3'-tert-butyl-5'-(2-methoxycarbonylethyl)-2'-hydroxyphenyl]-2H-benzotriazole with polyethylene glycol 300;
[R—CH$_2$CH$_2$—COO(CH$_2$)$_3$]$_2$, where R=3'-tert-butyl-4'-hydroxy-5'-2H-benzotriazol-2-ylphenyl.

Examples of sulfur-containing peroxide scavengers and sulfur-containing antioxidants of group r) are esters of 3,3'-thiodipropionic acid, such as the lauryl, stearyl, myristyl and tridecyl esters, mercaptobenzimidazole and the zinc salt of
2-mercaptobenzimidazole, zinc dibutyldithiocarbamate, dioctadecyl disulfide and pentaerythritol tetrakis(β-dodecylmercaptopropionate).

Examples of the 2-hydroxybenzophenones of group s) are the
4-hydroxy, 4-methoxy, 4-octyloxy, 4-decyloxy, 4-dodecyloxy,
4-benzyloxy, 4,2',4'-trihydroxy and 2'-hydroxy-4,4'-dimethoxy derivatives.

Examples of esters of unsubstituted or substituted benzoic acid of group t) are 4-tert-butylphenyl salicylate, phenyl salicylate, octylphenyl salicylate, dibenzoylresorcinol, bis(4-tert-butylbenzoyl)resorcinol, benzoylresorcinol,
2,4-di-tert-butylphenyl 3,5-di-tert-butyl-4-hydroxybenzoate, hexadecyl 3,5-di-tert-butyl-4-hydroxybenzoate, octadecyl
3,5-di-tert-butyl-4-hydroxybenzoate and
2-methyl-4,6-di-tert-butylphenyl 3,5-di-tert-butyl-4-hydroxybenzoate.

Examples of the acrylates of group u) are ethyl α-cyano-β,β-diphenylacrylate, isooctyl α-cyano-β,β-diphenylacrylate, methyl α-methoxycarbonylcinnamate, methyl α-cyano-β-methyl-p-methoxycinnamate, butyl α-cyano-β-methyl-p-methoxy-cinnamate and methyl α-methoxycarbonyl-p-methoxycinnamate.

Examples of the sterically hindered amines of group v) are
bis(2,2,6,6-tetramethylpiperidin-4-yl) sebacate,
bis(2,2,6,6-tetramethylpiperidin-4-yl) succinate,
bis(1,2,2,6,6-pentamethylpiperidin-4-yl) sebacate,
bis(1-octyloxy-2,2,6,6-tetramethylpiperidin-4-yl) sebacate,
bis(1,2,2,6,6-pentamethylpiperidin-4-yl)
n-butyl-3,5-di-tert-butyl-4-hydroxybenzylmalonate, the condensation product of
1-(2-hydroxyethyl)-2,2,6,6-tetramethyl-4-hydroxypiperidine and succinic acid, the condensation product of
N,N'-bis(2,2,6,6-tetramethylpiperidin-4-yl) hexamethylenediamine and 4-tert-octylamino-2,6-dichloro-1,3,5-triazine,
tris(2,2,6,6-tetramethylpiperidin-4-yl) nitrilotriacetate,
tetrakis(2,2,6,6-tetramethylpiperidin-4-yl) 1,2,3,4-butanetetracarboxylate, 1,1'-(1,2-ethylene)bis(3,3,5,5-tetramethylpiperazinone),
4-benzoyl-2,2,6,6-tetramethylpiperidine,
4-stearyloxy-2,2,6,6-tetramethylpiperidine,
bis(1,2,2,6,6-pentamethylpiperidin-4-yl) 2-n-butyl-2-(2-hydroxy-3,5-di-tert-butylbenzyl)malonate,
3-n-octyl-7,7,9,9-tetramethyl-1,3,8-triazaspiro[4.5]decane-2,4-dione, bis(1-octyloxy-2,2,6,6-tetramethylpiperidin-4-yl)
sebacate, bis(1-octyloxy-2,2,6,6-tetramethylpiperidin-4-yl) succinate, the condensation product of
2-chloro-4,6-bis(4-n-butylamino-2,2,6,6-tetramethyl-piperidin-4-yl)-1,3,5-triazine and
1,2-bis(3-aminopropylamino)ethane, the condensation product of
2-chloro-4,6-di(4-n-butylamino-1,2,2,6,6-pentamethylpiperidin-4-yl)-1,3,5-triazine and 1,2-bis(3-aminopropylamino)ethane,
8-acetyl-3-dodecyl-7,7,9,9-tetramethyl-1,3,8-triazaspiro [4.5]-decane-2,4-dione,
3-dodecyl-1-(2,2,6,6-tetramethylpiperidin-4-yl)pyrrolidine-2,5-dione,
3-dodecyl-1-(1,2,2,6,6-pentamethylpiperidin-4-yl) pyrrolidine-2,5-dione, a mixture of 4-hexadecyloxy- and
4-stearyloxy-2,2,6,6-tetramethylpiperidine, the condensation product of
N,N'-bis(2,2,6,6-tetramethylpiperidin-4-yl) hexamethylenediamine and 4-cyclohexylamino-2,6-dichloro-1,3,5-triazine, the condensation product of 1,2-bis(3-aminopropylamino)ethane and
2,4,6-trichloro-1,3,5-triazine,
4-butylamino-2,2,6,6-tetramethylpiperidine,
N-(2,2,6,6-tetramethylpiperidin-4-yl)-n-dodecylsuccinimide,
N-(1,2,2,6,6-pentamethylpiperidin-4-yl)-n-dodecylsuccinimide,
2-undecyl-7,7,9,9-tetramethyl-1-oxa-3,8-diaza-4-oxospiro [4.5]-decane, the condensation product of
7,7,9,9-tetramethyl-2-cycloundecyl-1-oxa-3,8-diaza-4-oxospiro-[4.5]decane and epichlorohydrin,
poly(methoxypropyl-3-oxy)-[4(2,2,6,6-tetramethyl) piperidinyl]-siloxane, polymer-analogous reaction products made from
4-amino-2,2,6,6-tetramethylpiperidine with maleic acid-/C$_{20}$–C$_{24}$-α-olefin copolymers, e.g. Uvinul® 5050H (BASF Aktiengesellschaft, Ludwigshafen), and, correspondingly thereto, polymer-analogous reaction products with
4-amino-1,2,2,6,6-pentamethylpiperidine (e.g. "methylated Uvinul® 5050H"), condensation products made from tetramethylolacetylenediurea and
4-amino-2,2,6,6-tetramethylpiperidine, e.g. Uvinul®4049H (BASF Aktiengesellschaft, Ludwigshafen), and, correspondingly thereto, condensation products with
4-amino-1,2,2,6,6-pentamethylpiperidine (e.g. "methylated Uvinul® 4049H") and also
N,N'-bis(2,2,6,6-tetramethylpiperidin-4-yl)-N,N'-bisformyl-1,6-di aminohexane, e.g. Uvinul®4050H (BASF Aktiengesellschaft, Ludwigshafen).

Examples of the oxamides of group w) are
4,4'-dioctyloxyoxanilide, 2,2'-diethoxyoxanilide,
2,2'-dioctyloxy-5,5'-di-tert-butoxanilide,
2,2'-didodecyloxy-5,5'-di-tert-butoxanilide,
2-ethoxy-2'-ethyloxanilide,
N,N'-bis(3-dimethylaminopropyl)oxamide,
2-ethoxy-5-tert-butyl-2'-ethoxanilide and its mixtures with
2-ethoxy-2'-ethyl-5,4'-di-tert-butoxanilide, and also mixtures of ortho- and para-methoxy-disubstituted oxanilides and mixtures of ortho- and para-ethoxy-disubstituted oxanilides.

Examples of the 2-(2-hydroxyphenyl)-1,3,5-triazines of group x) are 2,4,6-tris(2-hydroxy-4-octyloxyphenyl)-1,3,5-triazine,
2-(2-hydroxy-4-octyloxyphenyl)-4,6-bis(2,4-dimethylphenyl)-1,3,5-triazine,
2-(2,4-dihydroxyphenyl)-4,6-bis(2,4-dimethylphenyl)-1,3,5-triazine,
2,4-bis(2-hydroxy-4-propyloxyphenyl)-6-(2,4-dimethylphenyl)-1,3,5-triazine,
2-(2-hydroxy-4-octyloxyphenyl)-4,6-bis(4-methylphenyl)-1,3,5-triazine,
2-(2-hydroxy-4-dodecyloxyphenyl)-4,6-bis(2,4-dimethylphenyl)-1,3,5-triazine,
2-(2-hydroxy-4-tridecyloxyphenyl)-4,6-bis(2,4-dimethylphenyl)-1,3,5-triazine,
2-[2-hydroxy-4-(2-hydroxy-3-butyloxypropoxy)phenyl]-4,6-bis-(2,4-dimethyl)-1,3,5-triazine,
2-[2-hydroxy-4-(2-hydroxy-3-octyloxypropoxy)phenyl]-4,6-bis-(2,4-dimethyl)-1,3,5-triazine,
2-[4-(dodecyloxy/tridecyloxy-2-hydroxypropoxy)-2-hydroxyphenyl]-4,6-bis(2,4-dimethylphenyl)-1,3,5-triazine,
2-[2-hydroxy-4-(2-hydroxy-3-dodecyloxypropoxy)phenyl]-4,6-bis-(2,4-dimethylphenyl)-1,3,5-triazine,
2-(2-hydroxy-4-hexyloxyphenyl)-4,6-diphenyl-1,3,5-triazine,
2-(2-hydroxy-4-methoxyphenyl)-4,6-diphenyl-1,3,5-triazine,
2,4,6-tris[2-hydroxy-4-(3-butoxy-2-hydroxypropoxy) phenyl]-1,3,5-triazine and
2-(2-hydroxyphenyl)-4-(4-methoxyphenyl)-6-phenyl-1,3,5-triazine.

Examples of costabilizers which may be used are iron compounds as described in WO 98/25872, in particular on pages 25 to 36. If these compounds are colored, this often being the case, their use is, of course, only possible if the intrinsic color is acceptable.

Another important factor, of course, is whether these iron compounds provide the property profile desired for the application sector. For example, certain requirements generally have to be fulfilled with respect to their thermal stability during processing and during subsequent use, their toxicity or non-toxicity, their volatility etc. However, the selection of possible compounds whose property profile is as desired is normally simple, since the physical and chemical data for the compounds is generally known or can easily be determined.

Examples of polymers which can be stabilized by the compounds of the invention, or the compounds prepared according to the invention, are:
polymers of mono- and diolefins, e.g. low- or high-density polyethylene, linear poly-1-butene, polyisoprene, polybutadiene, and also copolymers of mono- or diolefins, or mixtures of the polymers mentioned;
copolymers of mono- or diolefins with other vinyl monomers, e.g. ethylene-alkyl acrylate copolymers, ethylene-alkyl methacrylate copolymers, ethylene-vinyl acetate copolymers, or ethylene-acrylic acid copolymers;
polystyrene;
copolymers of styrene or a-methylstyrene with dienes or with acrylic derivatives, e.g. styrene-butadiene, styrene-acrylonitrile, styrene-ethyl methacrylate, styrene-butadiene-ethyl acrylate, styrene-acrylonitrile-methacrylate;
ABS polymers, MBS polymers or similar polymers;
halogen-containing polymers, e.g. polyvinyl chloride, polyvinyl fluoride, polyvinylidene fluoride, and also copolymers of these;

polymers which derive from α,β-unsaturated acids or from derivatives of these, for example polyacrylates, polymethacrylates, polyacrylamides and their polyacrylonitriles;

polymers which derive from unsaturated alcohols or amines, or from their acrylic derivatives or acetals, e.g. polyvinyl alcohol and polyvinyl acetate;

polyurethanes, polyamides, polyurea, polyesters, polycarbonates, polysulfones, polyether sulfones and polyether ketones.

According to the invention, it is also possible to use the compounds of the invention, where appropriate with the addition of one or more of the abovementioned additives, to stabilize coating materials, especially those coating materials and finishes which are exposted to a high level of environmental influences, such as sunlight or heat. Examples of these are coating materials for outdoor painting applications or industrial finishes or vehicle finishes, or else coatings for stoved finishes, especially automotive finishes.

The compounds of the invention, or the compounds prepared according to the invention, may be in solid or dissolved form when added to the coating material. It is therefore particularly advantageous that they generally have good solubility in coating systems.

The piperidine derivatives of the invention, or prepared according to the invention, and having the formula I are preferably used for stabilizing polyolefins, in particular ethylene polymers or propylene polymers, or for stabilizing polyurethanes or polyamides.

Also claimed within the scope of the present invention is the stabilized organic material which comprises piperidine derivatives of the invention, or prepared according to the invention, and having the formula I.

EXAMPLE

Synthesis of the Stabilizer

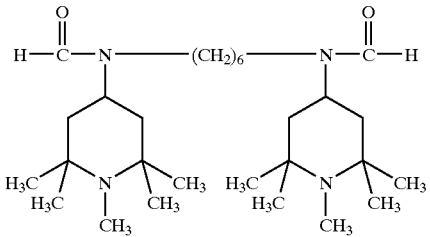

337 g of the Uvinul® 4050H stabilizer (BASF Aktiengesellschaft, Ludwigshafen; formula indicated at earlier point) are dissolved in 1200 ml of xylene in a 2 l flask with flat ground flange and with anchor stirrer and water separator. 227 g of 37% strength formalin solution are added, the mixture is heated to 80° C., and within a period of 55 minutes 86 g of formic acid are added at 80–85° C., with nitrogen flushing. There is vigorous evolution of carbon dioxide. The mixture is slowly heated to 95° C. and stirring is continued for 2 h, and during this process about 130 g of water is separated. After cooling to an internal temperature of 80° C., 600 ml of water are added. 1.2 l of xylene are then removed by azeotropic distillation at a bath temperature of 140–160° C. The product crystallizes on cooling to room temperature. It is 45 freed from mother liquor and dried in vacuo. Yield: 228 g Performance Testing:

Methylated Uvinul® 4050H prepared as in the example above, and its starting material Uvinul® 4050H (comparative stabilizer), each had a concentration of 0.5% by weight, were mixed with the ABS grade Terluran 877 T (BASF Aktiengesellschaft, Ludwigshafen) and with 2% by weight of $TiO_2$ (the concentration data being based on the entire mixture) in an intensive mixer, and then passed through a laboratory extruder at 240° C. for homogenization and pelletization. The pellets produced were injection molded to give test specimens of 2 mm thickness, and these were aged at 90° C. in a circulating-air oven. The yellowing (Yellowness Index, YI) was measured after 0, 250, 500 and 750 h of aging in the oven.

The YI is a measure of the effectiveness of the stabilizer. A smaller value here indicates that the stabilizer has better action.

YI after hours of aging in the oven at 90° C.:

|  | 0 h | 250 h | 500 h | 750 h |
|---|---|---|---|---|
| Uvinul ® 4050 H | 10.7 | 11.6 | 13.4 | 20.6 |
| methylated Uvinul ® 4050 H | 10.4 | 10.6 | 11.2 | 13.7 |

The methylated Uvinul® 4050H of the invention has a markedly better duration of stabilization than Uvinul® 4050H.

We claim:

1. A 4-formylamino-N-methylpiperidine derivative of formula (I)

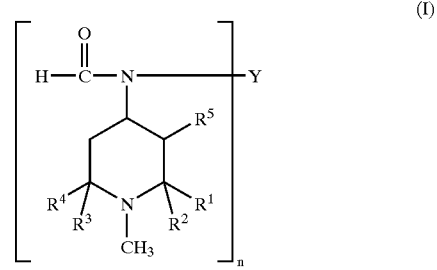

where $R^1$, $R^2$, $R^3$ and $R^4$, independently of one another, are $C_1$–$C_4$-alkyl, or $R^1$ and $R^2$, or $R^3$ and $R^4$, together are tetramethylene or pentamethylene, $R^5$ is hydrogen or $C_1$–$C_4$-alkyl, and n is 1 or 2, wherein when n=1:

Y is hydrogen, $C_1$-$C_{22}$-alkyl, $C_2$–$C_{22}$-alkenyl, $C_3$-$C_{12}$-cycloalkyl, or bicycloalkyl; cyano-, hydroxyl- or $C_1$–$C_4$-alkoxycarbonyl-substituted $C_1$–$C_{22}$-alkyl; ethereal-oxygen-, nitrogen- or sulfur-interrupted, unsubstituted or hydroxyl-substituted $C_4$-$C_{22}$-alkyl; unsubstituted or $C_1$–$C_4$-alkyl-, fluorine-, chlorine-, $C_1$–$C_4$-alkoxy or di($C_1$–$C_4$-alkyl)amino-substituted $C_7$–$C_{22}$-phenyl- or diphenylalkyl; unsubstituted or $C_1$–$C_4$-alkyl- or $C_1$–$C_4$-alkoxycarbonyl-substituted phenyl; a radical of the formula

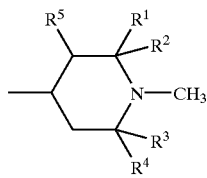

where,
R$^1$, R$^2$, R$^3$ and R$^4$, independently of one another, are C$_1$–C$_4$-alkyl, or R$^1$ and R$^2$, or R$^3$ and R$^4$, together are tetramethylene or pentamethylene,
R$^5$ is hydrogen or C$_1$–C$_4$-alkyl,
or C$_1$–C$_{22}$-alkyl containing heterocyclic radicals, and when n=2:
Y is C$_1$–C$_{22}$-alkylene, C$_5$–C$_{22}$-cycloalkylene, C$_8$–C$_{14}$-phenylalkylene, phenylene, or C$_4$–C$_{30}$-alkylene interrupted by ethereal oxygen, by nitrogen, by sulfur, or by five- or six-membered heterocycles.

2. The piperidine derivative of formula I as claimed in claim 1, where R$^1$, R$^2$, R$^3$ and R$^4$ are methyl.

3. The piperidine derivative of formula I as claimed in claim 1, where R$^5$ is hydrogen.

4. The piperidine derivative of formula I as claimed in claim 1, where n is 2.

5. The piperidine derivative of formula I as claimed in claim 4, where Y is C$_2$–C$_{22}$-alkylene.

6. The piperidine derivative of formula I as claimed in claim 4, where Y is C$_1$–C$_{12}$-alkylene.

7. A process for preparing piperidine derivative of formula I as claimed in claim 1, which comprises
reacting compounds of formula I'

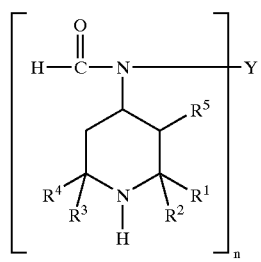

in an organic solvent, emulsification medium or suspension medium whose boiling point at 1.013 bar is at least 70° C., with formaldehyde, and then
reacting with formic acid at from 70° C. to not more than the boiling point at 1.013 bar of the solvent, emulsification medium or suspension medium.

8. A composition comprising an organic material and one or more piperidine derivatives of formula I as claimed in claim 1.

9. A method comprising
mixing the piperidine derivative claimed in claim 1 with an organic material.

10. The method as claimed in claim 9, wherein the piperidine derivative is mixed with the organic material in an amount of from 0.01 to 5% by weight based on the weight of the organic material.

11. A method comprising
mixing a piperidine derivative prepared by the process as claimed in claim 7 with an organic material.

12. The method as claimed in claim 10, wherein the piperidine derivative is mixed with the organic material in an amount of from 0.01 to 5% by weight based upon the weight of the organic material.

13. A method comprising
mixing the piperidine derivative as claimed in claim 1 with a coating material.

14. The method as claimed in claim 13, wherein the piperidine derivative is mixed with the coating material in an amount of from 0.01 to 5% by weight based upon the weight of the coating material.

15. A method comprising
mixing a piperidine derivative prepared by the process as claimed in claim 7 with a coating material.

16. The method as claimed in claim 15, wherein the piperidine derivative is mixed with the coating material in an amount of from 0.01 to 5% by weight based upon the weight of coating material.

17. A method comprising
mixing the piperidine derivative as claimed in claim 1 with a stabilizer.

18. A method comprising
mixing the piperidine derivative prepared by the process as claimed in claim 7 with a stabilizer for wood surfaces.

19. A composition comprising an organic material and a piperidine derivative prepared by the process as claimed in claim 7.

* * * * *